(12) United States Patent
Klug et al.

(10) Patent No.: US 9,506,911 B2
(45) Date of Patent: Nov. 29, 2016

(54) DEVICE HAVING AN INTERNAL AND AN EXTERNAL FUNCTIONAL ELEMENT AND METHOD FOR THE PRODUCTION THEREOF

(71) Applicants: Ulrich Klug, Hannover (DE); Andre Neumeister, Kamen (DE); Detlefr Rath, Neustadt (DE)

(72) Inventors: Ulrich Klug, Hannover (DE); Andre Neumeister, Kamen (DE); Detlefr Rath, Neustadt (DE)

(73) Assignee: Laser Zentrum Hannover e.V., Hannover (DE)

( * ) Notice: Subject to any disclaimer, the term of this patent is extended or adjusted under 35 U.S.C. 154(b) by 0 days.

(21) Appl. No.: 14/133,728

(22) Filed: Dec. 19, 2013

(65) Prior Publication Data
US 2014/0178919 A1 Jun. 26, 2014

Related U.S. Application Data

(60) Provisional application No. 61/740,655, filed on Dec. 21, 2012.

(51) Int. Cl.
*G01N 33/50* (2006.01)
(52) U.S. Cl.
CPC .................... *G01N 33/5005* (2013.01)
(58) Field of Classification Search
CPC .................................................. G01N 33/5005
See application file for complete search history.

(56) References Cited

U.S. PATENT DOCUMENTS 4,988,619 A * 1/1991 Pinkel .............................. 435/30
5,985,216 A 11/1999 Rens et al.

FOREIGN PATENT DOCUMENTS

DE 102011006080 A1 9/2012
WO 2009/151624 A1 6/2009

OTHER PUBLICATIONS

Kachel et al., "Uniform lateral orientation, caused by flow forces of flat particles in flow-through systems", The Journal of Histochemistry and Cytochemistry, 1977, pp. 774-780, vol. 27, No. 7.

*Primary Examiner* — Rosanne Kosson
(74) *Attorney, Agent, or Firm* — Whitham, Curtis, Christofferson & Cook, P.C.

(57) ABSTRACT

The present invention provides a device having an internal and an external functional element for producing a fluid stream having a core stream and an sheath stream. The device having an internal and an external functional element is distinguished by an internal component for shaping a core stream, an external functional element having a section for guiding an sheath stream and a section for focusing the sheath stream having core stream at the free end of the functional element, wherein the device having an internal and an external functional element is formed in such a manner that the functional element for shaping the core stream is spatially separated from the external functional element having a section for focusing the sheath stream and/or the section for guiding the sheath stream. In a further aspect, an apparatus for separating particles having this device having an internal and an external functional element is provided. In particular, this is a flow-cytometry apparatus in this case. Furthermore, the present application is directed to a method for separating particles with the aid of this device, in particular to a method for separating living isolated cells such as germ cells. Finally, a method for the production of such a device is provided.

10 Claims, 2 Drawing Sheets

Figure 1
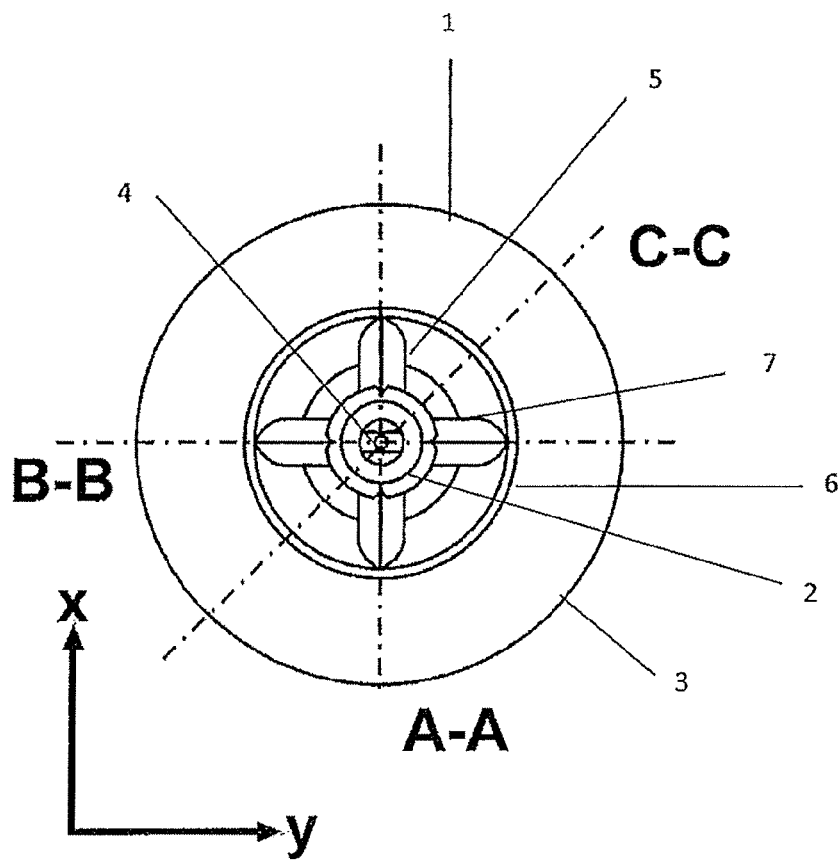
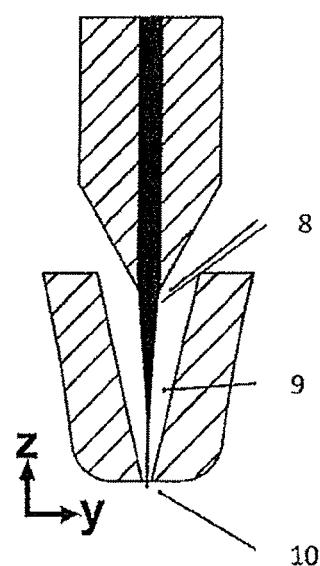
Figure 2

Figure 3a
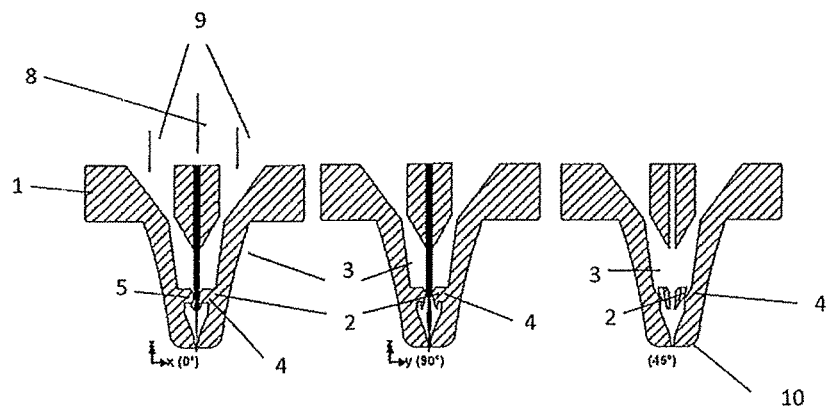
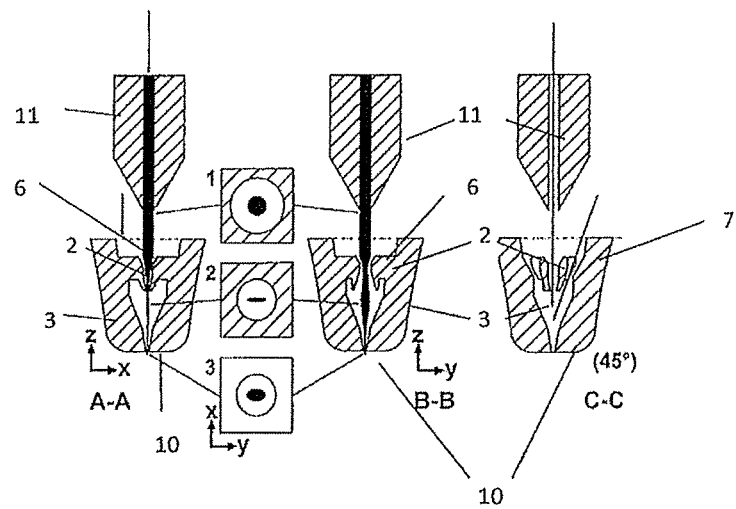
Figure 3b
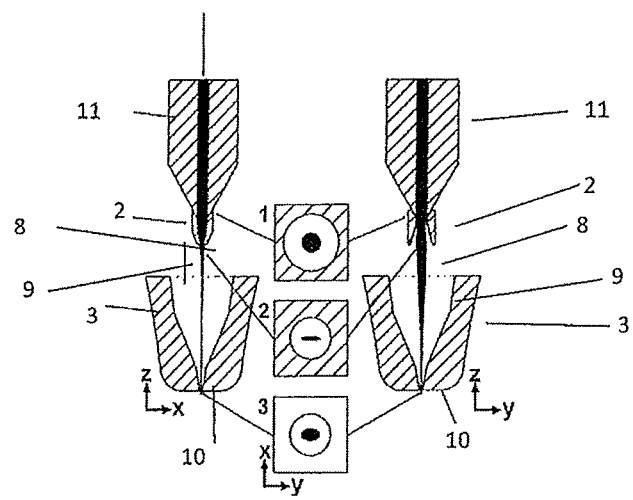
Figure 4

DEVICE HAVING AN INTERNAL AND AN EXTERNAL FUNCTIONAL ELEMENT AND METHOD FOR THE PRODUCTION THEREOF

The present invention provides a device having an internal and an external functional element for producing a fluid stream having a core jet and an envelope jet. The device having an internal and an external functional element is distinguished by an internal component for shaping a core jet, an external functional element having a section for guiding an envelope jet and a section for focusing the envelope jet having core jet at the free end of the functional element, wherein the device having an internal and an external functional element is formed in such a manner that the functional element for shaping the core jet is spatially separated from the external functional element having a section for focusing the envelope jet and/or the section for guiding the envelope jet. In a further aspect, an apparatus for separating particles having this device having an internal and an external functional element is provided. In particular, this is a flow-cytometry apparatus in this case. Furthermore, the present application is directed to a method for separating particles with the aid of this device, in particular to a method for separating living isolated cells such as germ cells. Finally, a method for the production of such a device is provided.

BACKGROUND OF THE INVENTION

The separation and selection of particles, in particular living cells such as spermatozoa, is the subject matter of many methods. In particular, the qualitative and quantitative, but also cost-effective separation and selection of spermatozoa, the so-called "sexing", plays an important role here. In this case, this relates to the sex-specific sorting of spermatozoa, which is assigned great economic significance in the field of livestock.

In the field of livestock breeding and livestock reproduction, in particular of cattle, but also of pigs, sheep, poultry, or horses, the prior establishment of the sex of the offspring is advantageous. Flow cytometers, as are commercially available, are conventionally used for the sex-specific sorting of sperm. To differentiate the X and Y chromosomal sperm, differences in the DNA content of the two types of sperm in comparison to one another are utilized, which can be determined by special detection capabilities of flow cytometers. On the basis of the known differences in the DNA content between sperm which contain the larger X-chromosome and those which contain the smaller Y-chromosome, for example, in the case of cattle by approximately 4%, it is possible to utilize this difference in the DNA content to determine the sex of the sperm, on the one hand, and to separate and select these sperm, on the other hand.

Fundamentally, the particles to be detected and selected are isolated in a fluid stream in flow cytometry, to then be selected accordingly on the basis of a determined signal. For this purpose, this is conventionally the signal of a DNA-specific fluorescent pigment, which is detected with the aid of excitation via a laser beam. Further desired particle properties, such as size, etc., can be determined with the aid of the detectors. This is conventionally performed via the determination of the scattered light of the incident laser light. With the aid of the detectors, corresponding measuring signals are generated, which permit a statement about the DNA content of the particles and also about the size and other properties of the particles. Separation and selection of the particles, in particular the sperm, is then carried out via a sorting device. A corresponding separation and selection is conventionally performed via a deflection in an electrical field of the droplets produced from a fluid stream. For this purpose, the fluid stream and therefore also the droplets produced therefrom are electrically charged to then be electrostatically deflected and selected accordingly during the passage through an electrical field.

In the case of sperm, the selection is performed based on the DNA content. The determination of the DNA content is also strongly dependent on the morphology of the cells, however, so that the orientation of the sperm can have an influence on the measured value of the DNA content.

Accordingly, it is necessary to provide those methods which permit an orientation of the cells, in order to improve the determination of the DNA content.

Improved nozzles for flow cytometers are described in WO 01/40765. Damage to the cell is to be prevented by the nozzle geometry described therein.

WO 2005/075629 describes a device for measuring oriented aspheric cells. For this purpose, a determination of the orientation of the sperm is carried out via a second light source.

Furthermore, nozzles or functional elements such as the injector for the core jet for producing a fluid stream are described, which do not have a round formation, but rather an ellipsoidal formation at the outlet.

To obtain the highest possible yield during the selection, the sperm are aligned such that the flat side of the sperm head is aligned perpendicular to the radiation to be detected. For this purpose, a specially designed nozzle geometry is used. This nozzle geometry permits the core jet containing the sperm to be focused hydrodynamically and simultaneously shaped elliptically by an externally enclosing, liquid envelope stream. The shaping is based on the principle that by way of the elliptical formation of the nozzle inner wall, which tapers toward the outlet, and the asymmetrical radial velocity gradients of the envelope stream, the core jet is also elliptically shaped and focused. In principle, the ellipsoidal shape of the core jet cross-section is thus applied pivoted by 90° in relation to the ellipsoidal shape of the nozzle wall. This results in a low sorting rate.

The object of the invention is to provide novel devices having an internal and an external functional element for producing a fluid stream, in particular nozzles for flow cytometers, which permit a significantly increased sorting rate of particles, in particular living cells, such as spermatozoa.

BRIEF DESCRIPTION OF THE INVENTION

In a first aspect, a device having an internal and an external functional element for producing a fluid stream having a core jet and an envelope jet is provided, wherein the internal functional element has a section for shaping a core jet and the external functional element has a section for guiding an envelope jet and a section for focusing the envelope jet having core jet at the free end of the functional element. The device having an internal and an external functional element is distinguished in that the internal functional element having the section for shaping the core jet has a flow channel, through which the core jet is guided, and that the internal functional element is spatially separated from the external functional element having a section for focusing the envelope jet having the core jet and/or the section for shaping the envelope jet.

In a further aspect, an apparatus for the separation and selection of particles is provided according to the invention. This apparatus is an apparatus for the separation and selection of particles, which has a device having an internal and an external functional element for producing a fluid stream containing particles, an irradiation device which is oriented onto the fluid stream exiting from the device, a detector which is oriented onto the fluid stream and is configured to produce measuring signals, a control unit connected to the detector, which is configured to receive detection signals and to produce control signals for a selection unit, and a selection unit connected to the control unit, which is configured to receive the control signals, wherein preferably the irradiation device has a laser for generating laser radiation, the beam path of which is oriented onto the fluid stream, characterized in that a device according to the invention for producing a fluid stream having a core jet and an envelope jet is used.

Furthermore, a method for the selection of particles, in particular for the selection of mammalian spermatozoa, is provided, wherein the fluid stream containing particles is formed using the device according to the invention. Finally, a method for the production of a functional element having a flow channel, in particular a method for the production of a functional element for producing a fluid stream from a core jet and an envelope jet, as described according to the invention, is provided. This method is distinguished in that at least the internal functional element having the flow channel is produced by means of stereolithography.

DETAILED DESCRIPTION OF THE INVENTION

In a first aspect, the present application is directed to a device having an internal and an external functional element for producing a fluid stream having a core jet and an envelope jet having an internal functional element for shaping a core jet, an external functional element having a section for shaping an envelope jet and a section for focusing the envelope jet having core jet at the free end of the functional element, characterized in that the functional element for shaping the core jet has a flow channel, through which the core jet is guided, and it is spatially separated from the section for focusing the envelope jet having the core jet and/or the section for shaping the envelope jet.

It is presumed that improved sorting rates and more stable detection and separation of particles in a fluid stream, in particular a sex-specific sorting of sperm, are achieved in that the core jet shaping is carried out separately from the acceleration or the hydrodynamic focusing, respectively.

That is to say, in a first step the core jet, which contains the particles, in particular the spermatozoa, is shaped and subsequently the focusing of the core jet is performed by the circular envelope jet. By way of the separation of these two essential steps in the device according to the invention, specifically the shaping of the core jet and the hydrodynamic focusing, it is possible to achieve an orientation of the particles, in particular of non-rotationally symmetrical particles such as sperm, in the core jet. The circular envelope jet focuses the core jet, which is provided after passage through the flow channel, having the isolated and aligned cells.

The term "core jet" is understood in the present case as the fluid jet, which is completely enclosed by a second jet, the envelope jet. The composition of the core jet typically differs from that of the envelope jet, in particular the core jet contains particles to be analyzed and optionally to be selected. The core jet is conventionally produced using an injector. This injector conventionally has a needle-shaped element for this purpose.

The term "envelope jet" is understood in the present case as a fluid jet which completely envelops a second jet. The envelope jet conventionally does not contain any particles.

The terms "sperm" and "spermatozoa", which are used synonymously in the present case, are understood to mean both those which consist only of the head part, and also those which also have the middle part and tail part, i.e., complete sperm.

With the aid of the flow channel formed in the internal functional element, shaping of the core jet is possible, for example, into a noncircular shape such as an oval shape. The flow channel therefore permits an orientation of the particles present in the core jet, in particular the sperm. That is to say, it is preferable for the internal functional element having the section for shaping the core jet to have a cross-section adapted for the alignment of particles present in the core jet. This cross-section at the outlet of the flow channel of the internal functional element is particularly preferably an oval. The flow channel can have a different cross-section at the inlet than at the outlet. In particular, the cross-section in the inlet region can be round, while it has the desired shape, in particular an oval cross-section, in the outlet region. In particular, the inlet region of the internal functional element can be rotationally symmetrical, while the outlet of the internal functional element is non-rotationally symmetrical, specifically oval, in particular ellipsoidal. Oval is understood in the present case as a cross-section which is noncircular. A special form of oval is an ellipsoidal formation.

In one embodiment of the present invention, the flow channel of the internal functional element is formed in such a manner that the cross-sectional area of the flow channel does not change over the entire length, i.e., it is constant. In alternative embodiments, the cross-sectional area can shrink or enlarge in the direction of the outlet of the flow channel.

In a first embodiment, the device having an internal and an external functional element having a flow channel is formed in such a manner that the internal functional element having the flow channel, which element is arranged in the longitudinal axis of the device, is formed in an integrally joined, friction-locked, or formfitting manner with the external functional element. That is to say, the external functional element can be formed in one piece with the internal functional element having a flow channel or the internal functional element having a flow channel can accordingly be incorporated in the external functional element in an integrally joined, friction-locked, or formfitting manner.

In an alternative embodiment, the internal functional element having the flow channel is arranged on the injector. The internal functional element can be plugged onto the injector or connected in a formfitting or friction-locked manner to the injector in another manner. The device according to the invention can therefore consist of separately provided internal and external functional elements.

For example, the flow channel can be arranged centrally in relation to the longitudinal axis of the device having an internal and an external functional element. Depending on the stated object, however, an eccentric arrangement can also be possible. The internal functional element having the flow channel is preferably arranged in the lower section of the device. The internal functional element is preferably arranged in such a manner that the distance between the outlet of the internal functional element and the outlet of the external functional element is as small as possible, wherein the distance is sufficiently large to permit an acceleration and hydrodynamic focusing of the envelope jet having the core jet. The distance between the outlet of the internal functional element and the external functional element is preferably at least 300 μm, for example, at least 500 μm.

In some embodiments of the apparatus according to the invention, the flow channel is formed in such a manner that the envelope jet is brought into contact with the core jet substantially after the exit of the core jet from the internal functional element having the section for shaping the core jet, i.e., for example, after the exit from the flow channel.

After exiting from the internal functional element having the section for shaping the core jet, in particular after the exit from the flow channel, the core jet is provided substantially in the desired shape and is then subsequently accelerated and hydrodynamically focused using the envelope jet.

At the free end of the device having an internal and an external functional element, the cross-section of the outlet opening of the fluid stream having envelope jet and core jet provided therein is formed to be substantially circular. A circular formation of the fluid stream is particularly advantageous for promoting a stationary flow state in the free jet. Subsequent deviation of the set alignment of the cells is thus prevented.

The device according to the invention is in particular a nozzle for a flow cytometer. Embodiments thereof are described in greater detail in the explanation of the figures.

In a further aspect, the application is directed to the use of a device according to the invention for the shaping and focusing of a core jet, which contains particles, enveloped by an envelope jet. In particular, this device is suitable for the sex-specific sorting of sperm, such as cattle spermatozoa, by means of flow cytometry while using commercial flow cytometers.

In a further aspect, the application is therefore directed to an apparatus for the selection of particles, which has a device having an internal and an external functional element for producing a fluid stream containing particles, an irradiation device which is oriented onto the fluid stream exiting from the device, a detector which is oriented onto the fluid stream and is configured to produce measuring signals, a control unit connected to the detector, which is configured to receive measuring signals and to produce control signals, and a selection unit connected to the control unit, which is configured to receive the control signals. The irradiation device is preferably a laser radiation source for generating laser radiation. The device is characterized in that the device having an internal and an external functional element for producing a fluid stream having core jet and envelope jet is a device according to the invention.

The apparatus is preferably a flow cytometer having the device according to the invention. This apparatus is in particular one which permits a fluid stream to be produced from liquid droplets.

Corresponding apparatuses having the corresponding elements are known to a person skilled in the art.

The apparatus according to the invention conventionally furthermore has an oscillating body for generating a corresponding pressure oscillation for the fluid stream. An irradiation device, the radiation of which is oriented onto the fluid stream exiting from the nozzle, is arranged at a distance to the outlet opening of the device having an internal and an external functional element, in particular the nozzle, and a detector, the sensor surface of which is oriented onto the fluid stream, is arranged opposite to the irradiation device or at an angle thereto. Multiple detectors can be used to detect different or identical wavelengths. The detector is preferably an optical detector, the sensor surface of which is preferably provided with optical elements which are transmissive in all preselected wavelengths. In this manner, the detector can be set to a preselected wavelength, for example, if pigments are used, to the wavelength which is emitted by a pigment specific for the particle or a pigment or pigment conjugate associated with the particle. The irradiation device is preferably configured to emit an excitation wave to excite the emission of the radiation from a pigment or pigment conjugate, with which the particle is conjugated. This is also true in the case of the detection of scattered light.

Suitable pigments or pigment conjugates are known to a person skilled in the art. These are preferably fluorescent pigments or pigment conjugates, which specifically mark a part of the particles. This fluorescent pigment can either be, for example, one which intercalates with the DNA or one which is conjugated with a specific binding component, such as an antibody, a nucleic acid sequence, etc.

The detector is connected to a control unit, which records the measuring signals output by the detector, and which is configured to produce control signals for a selection unit based on these measuring signals and to transmit these control signals thereto. In general, a device for producing a fluid stream containing particles having a device according to the invention, from which the fluid stream exits, an irradiation device arranged at a distance thereto, and a detector assigned to the irradiation device, this detector being connected to a control unit, can correspond to the functionally-equivalent devices of a known flow cytometer, also designated as an FACS device.

A further aspect of the invention is a method for the separation and selection of particles, in particular of living cells such as sperm, by formation of a fluid stream containing particles, detection of a property of the particles in the fluid stream, production of a measuring signal specific for the properties, production of a control signal based on the measuring signal, control of a selection unit using control signals, and treatment of one of the particles as a function of the control signal, wherein the formation of the fluid stream containing particles is performed by a device according to the invention. In direct comparison to the prior art, it is possible with the aid of the method according to the invention to obtain significantly improved results in the sorting quality and rate. Furthermore, it is possible to achieve significantly higher sorting rates having stable detection, wherein the quality of the separated particles, in particular the selected sperm, can be improved. The obtained, selected X and Y sperm display improved qualities and higher purity.

The method according to the invention is particularly suitable for the selection or separation of living isolated cells, in particular germ cells. The germ cells are preferably those with the exception of human germ cells, in particular the germ cells are nonhuman mammalian spermatozoa. The method according to the invention is suitable in particular for the sex-specific sorting of sperm in the case of cattle, pigs, sheep, or other livestock.

Finally, a method for the production of a device having an internal and an external functional element having a flow channel in the internal functional element, in particular a device according to the invention for producing a fluid stream from a core jet and an envelope jet, is provided. This method is distinguished in that at least the internal functional element having the flow channel is produced by means of stereolithography.

The stereolithography method is known to a person skilled in the art. The functional element to be produced is built up in layers. Stereolithography is a technical embodiment of the layered construction method and permits the manufacturing of three-dimensional parts of very complex design. With the aid of micro-stereolithography, it is possible to provide the devices according to the invention having an internal and an external functional element. Typical monomer materials, as are used for stereolithography, can be used as materials. These are preferably those materials which cannot be electrically charged. Typical plastics, which have the required precision during the processing, can be used.

In the method according to the invention for the production of the internal functional element having a flow channel according to the invention, it is preferable in one embodiment that this internal functional element produced by means of micro-stereolithography is connected in a friction-locked, formfitting, or integrally joined manner to the external functional element.

The device according to the invention having an internal and an external functional element permits improvements in the sorting rates and the sorting quality and more stable detection of non-rotationally symmetrical particles such as sperm. It has also been shown that the obtained spermatozoa fractions can display less damage and higher motility and also fertility. The achievable higher sorting rates and increased viabilities are of great economic interest.

The invention will be described in greater detail on the basis of examples with reference to the figures. In each case the same reference signs are used in the figures for functionally-equivalent elements.

DESCRIPTION OF THE DRAWINGS

FIG. 1 is top view schematic of the device in the flow direction;

FIG. 2 is a schematic illustration showing the production of a fluid stream with a core stream and sheath;

FIG. 3a are cross-sectional schematics of an embodiment of the invention in the XZ dimension, the YZ dimension (rotated 90°), and rotated 45°;

FIG. 3b is an enlargement of a lower section of the views shown in FIG. 3a; and

FIG. 4 is a schematic of another embodiment of the invention in the XZ dimension and the YZ dimension (rotated 90°) showing various elements in XY cross-section.

DESCRIPTION

The schematic construction of a device according to the invention having an internal and an external functional element is shown in FIG. 1. The illustration shows a top view in the flow direction.

The device 1 having an internal functional element 2 and an external functional element 3 has a flow channel formed in the internal functional element. The internal functional element 2 having the flow channel 4 has webs 5 for the integrally joined connection to the external functional element 3. The flow channel 4 is arranged centered in the device 1.

The flow channel has a round cross-section in the inlet 6, while the cross-section at the outlet of the corresponding section, i.e., at the outlet of the flow channel, displays an oval cross-section. The envelope jet is guided through the free spaces 7 on the flow channel 4, to then be brought together with the core jet at the outlet of the flow channel. The core jet is produced according to known methods, for example, with the aid of a needle or a core jet injector and introduced into the internal functional element 2 having the contained flow channel 4 above the flow channel.

The external functional element 3 itself is formed tapering in the flow direction.

The flow channel can be formed at least sectionally tapering in the flow direction. Shaping of the core jet is performed in a nonround shape, preferably an oval shape, at the outlet of the flow channel. At the outlet of the flow channel, the core jet then comes into contact with the envelope jet flowing past externally on the flow channel. This envelope jet accelerates and focuses the fluid stream hydrodynamically up to the exit at the free end of the device.

In FIG. 2, the previous principle described in the prior art in devices for producing a fluid stream having a core jet and an envelope jet is shown. With the aid of a corresponding apparatus, the core jet 8 having the particles is introduced into the device and guided out together with the envelope jet 9 through the outlet of the functional element as a fluid stream having a core jet and an envelope jet in accelerated and focused form.

FIG. 3a shows a device 1 according to the invention having an internal functional element 2 and an external functional element 3. FIG. 3a shows cross-sections in the xz-direction and in the yz-direction, i.e., rotated by 90°, and also having a 45° rotation. FIG. 3b shows corresponding enlarged cross-sections of the lower section of the functional element, wherein the external functional element is only partially shown, and also the cross-sections of the fluid streams at the various identified positions. The specifications on the sectional planes correspond to those in FIG. 1.

The section for shaping a core jet in the form of a flow channel 4 is provided in the devices. The core jet is guided through the flow channel 4, while the envelope jet 9 is not conducted through the flow channel 4, but rather past it. In FIG. 3, the web 5 is shown, using which the section of the flow channel 4 of the internal functional element 2 is connected to the external functional element 3. Furthermore, the cross-section at the inlet and the cross-section at the outlet of the flow channel 4 can be recognized. The region in which the envelope stream can flow past the flow channel is also shown in the cross-section for 45°. As can be clearly recognized in comparison to the 0° view or 90° view, the cross-sections differ at the outlet out of the flow channel.

This is still more clear from FIG. 3b. An enlargement of the lower section of the functional element at 0°, 45°, and 90° is shown here. In the 0° view, i.e., xz-direction, the outlet is very narrow, while in the 90° view, i.e., the yz-direction, the outlet is wider, to thus obtain an oval cross-section of the outlet of the flow channel while maintaining the cross-sectional area of the flow channel. This is clear in the cross-section of the fluid stream identified with 2. In the cross-section of the fluid stream identified with 1, it can be seen that the inlet 6 of the flow channel has a substantially round cross-section. By way of the corresponding formation of the flow channel, the core jet is accordingly brought into an oval shape at the outlet. Subsequently, acceleration and focusing occur in the adjoining region by way of the envelope stream flowing past. At the free end 10 of the functional element, in which the fluid stream made of envelope stream and core stream exits, it can be seen that the exiting fluid stream itself is rotationally symmetrical, while the core jet maintains its oval cross-section and does not twist. It is thus possible to introduce the non-rotationally symmetrical particles, such as the sperm, in aligned form into the fluid stream for selection.

FIG. 4 shows a further embodiment of the present invention. The internal functional element 2 of the device 1 according to the invention is arranged on the injector 11, which can be in the form of a needle, for example. The internal functional element 2 having the flow channel 4 is arranged in a friction-locked or formfitting manner on the injector 11. As in FIG. 3, views in the xz-direction and yz-direction are shown. The formation of the oval core jet in the round envelope jet at the outlet of the external functional element 3 can be clearly recognized.

A higher sorting rate having improved detection and improved viability can thus be achieved according to the invention.

The invention claimed is:

1. A device having an internal functional element and an external functional element for producing a fluid stream having a core stream and a sheath stream, wherein the internal functional element shapes the core stream, wherein the external functional element has a section for guiding the sheath stream and a section for focusing the sheath stream at the free end of the external functional element, wherein the internal functional element for shaping the core stream has a flow channel, through which the core stream is guided, wherein the internal functional element is spatially separated from the external functional element and wherein the cross-section perpendicular to the flow channel at the outlet of the internal functional element is not circular.

2. The device according to claim 1, wherein the cross-section perpendicular to the flow channel at the outlet of the internal functional element is section is oval.

3. The device according to claim 1, wherein the internal functional element is arranged in the longitudinal axis of the device, and wherein the internal functional element is formed in an integrally joined, friction-locked, or formfitting manner with the external functional element.

4. The device according to claim 1, wherein the internal functional element is arranged in a friction-locked or form-fitting manner at the lower end of an injector to form the core stream.

5. The device according to claim 1, wherein the sheath stream is brought into contact with the core stream substantially after the exit of the core stream from the flow channel for shaping the core stream.

6. The device according to claim 1, wherein the cross-section of the external functional element at the free end is substantially round.

7. The device according to claim 1, wherein the device is a nozzle for a flow cytometer.

8. The device according to claim 1 wherein the core stream contains particles.

9. An apparatus for the selection of particles, which has a device having
a) an internal functional element and
b) an external functional element for producing a fluid stream containing particles,
c) an irradiation device which is oriented onto the fluid stream exiting from the functional elements,
d) a detector which is oriented onto the fluid stream and is configured to produce measuring signals,
e) a control unit connected to the detector, which is configured to receive measuring signals and to produce control signals for a particle selection unit, and
f) the particle selection unit, wherein the particle selection unit is connected to the control unit, which is configured to receive the control signals, wherein the irradiation device has a laser for generating laser radiation, the beam path of which is oriented onto the fluid stream, and wherein the device is the device according to claim 1.

10. The apparatus according to claim 9, wherein the apparatus is configured to produce a fluid stream from liquid droplets.

* * * * *

UNITED STATES PATENT AND TRADEMARK OFFICE
CERTIFICATE OF CORRECTION

PATENT NO. : 9,506,911 B2  
APPLICATION NO. : 14/133728  
DATED : November 29, 2016  
INVENTOR(S) : Klug et al.

Page 1 of 1

It is certified that error appears in the above-identified patent and that said Letters Patent is hereby corrected as shown below:

On the Title Page

Item (72), the third inventor's name should be corrected to read "Detlef Rath"

Signed and Sealed this
Fourteenth Day of February, 2017

Michelle K. Lee
*Director of the United States Patent and Trademark Office*